United States Patent [19]

LaCount

[11] Patent Number: 5,204,270
[45] Date of Patent: Apr. 20, 1993

[54] MULTIPLE SAMPLE CHARACTERIZATION OF COALS AND OTHER SUBSTANCES BY CONTROLLED-ATMOSPHERE PROGRAMMED TEMPERATURE OXIDATION

[76] Inventor: Robert B. LaCount, 403 Arbor Ct., Waynesburg, Pa. 15370

[21] Appl. No.: 692,981

[22] Filed: Apr. 29, 1991

[51] Int. Cl.$^5$ .................... G01N 25/24; G01N 31/12; G01N 1/10; G01J 3/08
[52] U.S. Cl. .................... 436/157; 250/343; 250/373; 356/246; 422/78; 422/80; 422/82.05; 436/155; 436/159; 436/160; 436/165
[58] Field of Search .............. 422/68.1, 78, 80, 82.05, 422/91; 436/155, 157, 159-160, 165; 356/246, 410; 250/343, 373

[56] References Cited

U.S. PATENT DOCUMENTS

| | | | |
|---|---|---|---|
| 3,020,795 | 2/1962 | McKinney et al. | 356/246 |
| 3,428,433 | 1/1969 | Ehrenberger et al. | 422/78 |
| 3,784,359 | 1/1974 | Parth | 422/79 |
| 3,838,972 | 10/1974 | Richards et al. | 436/100 |
| 3,985,505 | 10/1976 | Bredeweg et al. | 436/160 |
| 4,011,451 | 3/1977 | Nelson | 250/343 |
| 4,238,198 | 12/1980 | Swaim et al. | 436/120 |
| 4,736,103 | 4/1988 | Nelson et al. | 250/343 |
| 4,824,790 | 4/1989 | Carangelo et al. | 422/80 |
| 4,845,040 | 7/1989 | Moon et al. | 422/78 |
| 5,054,920 | 10/1991 | Doyle | 356/246 |

FOREIGN PATENT DOCUMENTS

| | | | |
|---|---|---|---|
| 58-195150 | 11/1983 | Japan | 422/78 |
| 1273792 | 11/1986 | U.S.S.R. | 422/80 |

OTHER PUBLICATIONS

LaCount et al., "Coal Characterization by Programmed-Temperature Oxidation", Electric Power Research Institute, 1-13 (U.S.A. 1991).
LaCount et al., "Construction and Operation of a Controlled-Atmosphere . . .", Pittsburgh Energy Technology Center, 2-22 (U.S.A. 1983).
LaCount et al., "Thermal Oxidative Degradation of Coal . . .", New Approaches in Coal Chemistry, 415-426 (U.S.A. 1981).
Stock et al., "Sulfur Distribution in American Bituminous Coals", Energy and Fuels, 3:651-661 (U.S.A. 1989).
Friedman, "Sulfur Analysis of Coal-A Critical Evaluation", Electric Power Research Institute, 3-12 (U.S.A. 1990).

(List continued on next page.)

Primary Examiner—James C. Housel
Assistant Examiner—Arlen Soderquist
Attorney, Agent, or Firm—James C. Wray

[57] ABSTRACT

A furnace with two hot zones holds multiple analysis tubes. Each tube has a separable sample-packing section positioned in the first hot zone and a catalyst-packing section positioned in the second hot zone. A mass flow controller is connected to an inlet of each sample tube, and gas is supplied to the mass flow controller. Oxygen is supplied through a mass flow controller to each tube to either or both of an inlet of the first tube and an intermediate portion between the tube sections to intermingle with and oxidize the entrained gases evolved from the sample. Oxidation of those gases is completed in the catalyst in each second tube section. A thermocouple within a sample reduces furnace temperature when an exothermic condition is sensed within the sample. Oxidized gases flow from outlets of the tubes to individual gas cells. The cells are sequentially aligned with an infrared detector, which senses the composition and quantities of the gas components. Each elongated cell is tapered inward toward the center from cell windows at the ends. Volume is reduced from a conventional cell, while permitting maximum interaction of gas with the light beam. Reduced volume and angulation of the cell inlets provide rapid purgings of the cell, providing shorter cycles between detections. For coal and other high molecular weight samples, from 50% to 100% oxygen is introduced to the tubes.

23 Claims, 7 Drawing Sheets

OTHER PUBLICATIONS

LaCount et al., "Sulfur in Coal by Programmed-Temperature Oxidation", Fuel; The Science and Technology of Fuel and Energy, 66:909–913 (U.S.A. 1987).
IR/FTIR Accessories and Supplies Catalog, Buick Scientific, 15 (U.S.A. 1990).
Infrared Accesssories and Supplies, Spectra Tech, 32–33 (U.S.A. 1990).
IR/FTIR, Spectra Tech, 6–7 (U.S.A. 1990).
Perkin Elmer–Infrared Spectroscopy Supplies Catalog, PE Express, 26–27 (U.S.A. 1989).
Calkins, "Investigation of Organic Sulfur–Containing Structures in Coal by Flash Pyrolysis Experiments", Energy and Fuels, 1:59–64 (U.S.A. 1987).
Boudou, "Identification of Some Sulphur Species in a High Organic Sulphur Coal", Fuel, 66:1558–1568 (1987).
Boudou et al., "Continuous Gas Detection During Heating of Coal and Kerogen", New Methodologies for Coal Characterization, 1–2 and 4–5 (France, undated).
Boudou, "Determination of the Nature of Organic Sulphur in a High Organic Sulphur Coal", Internal Conference on Coal Science, 13–14 (France, 1987).
Fixari et al., "Oxidative Pyroanalysis: Elemental Analysis in Volatile and Nonvolatile Fractions of Coals . . .", Fuel, 69:851–855 (France, 1990).
Bloodworth et al., "Thermomagnetometry and Evolved Gas Analysis . . .", Thermochimica Acta, 93:745–747 (Netherlands, 1985).
Solomon et al., "Analysis of the Argonne Premium Coal Samples . . .", Energy and Fuels, 4:319–333 (U.S.A. 1990).
Carangelo et al., "Application of TG-FT-i.r. to Study Hydrocarbon Structure and Kinetics", Fuel, 66:960–967 (U.S.A. 1987).
Carangelo et al., "Quantitative Evolved Gas Analysis From an Indianhead Zap Lignite", Advanced Fuel Research, 1–3 (U.S.A., undated).
Whelan, "Thermogravimetric Fourier Transform Infrared Spectroscopy . . .", Energy and Fuels, 2:65–73 (U.S.A. 1987).

MULTIPLE SAMPLE CHARACTERIZATION OF COALS AND OTHER SUBSTANCES BY CONTROLLED-ATMOSPHERE PROGRAMMED TEMPERATURE OXIDATION

BACKGROUND OF THE INVENTION

This invention concerns high molecular weight substance analysis and gas analysis apparatus and methods.

A problem with coal analysis is that exothermic reactions obscure results. Mixing coal with tungsten trioxide as a diluent helps. Low oxygen levels help to retard the exothermic reactions.

Work by the inventor has been centered around a controlled oxidation of coal as the temperature was gradually increased. Six years of studies and over 220 experiments resulted in a method showing some resolution (qualitative analysis) of the sulfur dioxide evolution from coal (diluted with tungsten trioxide) during oxidation with slowly increasing temperature. The results looked promising enough to continue the work. A quantitative system was assembled and continues to function today after well over 500 Runs.

The system works well, but conditions were not good enough to resolve the sulfur dioxide resulting from the pyritic sulfur and the second occurrence of organic sulfur detected from coal. The pyritic sulfur was oxidized just before the higher temperature organic sulfur, and much of the peak overlapped with the organic sulfur peak. That seriously limited the usefulness of that instrument in characterizing the amounts of pyritic and organic sulfur in coal or in providing a potential one step analysis method of the organic, inorganic and total sulfur in coal. Attempts continued to improve the instrument and to find conditions to resolve the sulfur dioxide evolved from oxidation of pyrite and organic sulfur in coal. That finally led to an all out attempt to find better reaction conditions.

A need continues to exist for apparatus for a systematic analysis of coal, particularly for forms of its sulfur content, and to analyze other substances and particularly high molecular weight substances.

Existing gas analysis cells have large volumes. Consequently a large volume of gas must be flowed into and out of a cell before a new significant reading may be taken. Quantities of available gases make purging inconvenient, wasteful and time consuming.

A need exists for analysis cells which may be readily filled, read and purged.

SUMMARY OF THE INVENTION

In the present invention, a furnace with two hot zones holds multiple analysis tubes. Each tube has a separable sample-packing section positioned in the first hot zone and a catalyst-packing section positioned in the second hot zone. A mass flow controller is connected to an inlet of each sample packing tube, and gas is supplied to the mass flow controller. Oxygen is supplied through a mass flow controller to each tube to either or both of an inlet of the first tube and an intermediate portion between the tube sections to intermingle with and oxidize the entrained gases evolved from the sample. Oxidation of those gases is completed in the catalyst in each second tube section. A thermocouple within the catalyst pack controls the temperature of the second hot zone, which remains substantially fixed. A thermocouple within at least one of the sample packings controls the uniform increase of temperature in the first hot zone, reducing the added heat immediately when an exothermic condition is sensed within the sample. Oxidized gases flow from outlets of the tubes to individual gas cells, and the gas flows through and out of the cells. The cells are sequentially periodically aligned with an infrared detector, which senses the composition and quantities of the gas components. Each elongated cell is tapered inward toward the center from cell windows at the end. Each cell contains a volume reduced from a conventional cell, while permitting maximum interaction of gas with the light beam. Reduced volume and angulation of the cell inlets provide rapid purgings of the cell, providing shorter cycles between detections. For coal and other high molecular weight samples, oxygen makes up from 50% to 100% of the gas introduced into the tubes.

This invention provides instruments and analysis equipment for a multi-sample by controlled-atmosphere programmed-temperature oxidation.

Before conception of the invention, a problem existed in determining whether sulfur was present in organic or inorganic compounds, for example in inorganic pyrite, which is iron disulfide. Exothermic reactions obscured results. The inventor experimented with gradually changing the oxygen concentration from 10% in argon to 16% in argon. A slight shift of the pyritic sulfur toward evolution at a higher temperature was noticed under those conditions. Continued increasing of the concentration to 20% and finally to 100% oxygen surprisingly improved results. The 100% oxygen experiment indicated that the pyritic sulfur evolution was moved to higher temperature and was evolved after the higher temperature organic sulfur peak, permitting both peaks to be resolved.

Further work showed that celite or other silica products such as silicic acid, silica gel, and synthetic silicas when used as diluents for the coal resulted in a more highly resolved pyrite evolution peak compared to tungsten trioxide, a previous diluent.

This invention provides use of the higher oxygen concentration ranges (50%–100%) and the use of tungsten trioxide, zirconium dioxide, silicon dioxide products, preferably celite, and other metal oxides as diluents. The invention also provides the use of metal oxides or other catalysts to oxidize organic compounds to oxides of carbon, hydrogen, sulfur and nitrogen. The metal oxides or other catalysts must not interact, absorb and re-emit, the oxide gases produced in the oxidation reaction.

The technique of the invention can be used to characterize coals, oilshales, carbon deposits on refinery and other catalysts, polymers, and other high molecular weight materials. In addition to the sulfur dioxide evolution profiles, the carbon dioxide, water, and nitrogen dioxide profiles are obtained. This allows characterization of the carbon, sulfur, hydrogen, and nitrogen in the material tested and analysis for those elements in the material.

The present invention is suited to resolve the gases evolved from the pyritic and the more oxidatively resistant organic sulfur in the material oxidized. The best conditions are produced in 100% oxygen with a silica product such as celite as a diluent for the material being oxidized. Preferably particle size of solids being oxidized and diluent are about -60 mesh or smaller. Preferably the diluent and the sample substance are well mixed and are uniformly distributed. However, high oxygen concentrations such as 50%–100% oxygen and other diluents such as silicic acid, silica gel, synthetic silicas, tungsten trioxide, zirconium dioxide, and other metal oxides may be used.

The technique is applicable to characterizing many substances, such as for example coals, treated coals, oil shales, polymers, carbon deposits on refinery and other catalysts, and other high molecular weight substances. The diluent or a screen may follow the sample. Preferably finely divided quartz wool previously heat treated at about 1100° C. is positioned upstream and downstream of the sample to hold the sample in position. Preferably quartz rods held in place by quartz wool are inserted in any void in the sample and catalyst tubes to reduce internal volume and promote flow-through of the evolved gases.

The invention evolves a material from the sample and oxidizes the evolved material.

When run in the oxidation mode, most of the oxidation occurs in the sample. The second tube and the catalyst complete the oxidation and establish $SO_2$—$SO_3$ equilibrium.

Characterizing the substances under the oxidizing conditions described above is one of the objects of the invention. The evolved gas concentration versus time and/or temperature profiles for carbon dioxide, sulfur dioxide, nitrogen dioxide, and water are unique. Additionally, analyses for the amount of carbon, sulfur, nitrogen, and hydrogen in the sample oxidized are obtained by calculations based on the evolved gases.

The instrument can also be used in a pyrolysis mode where an inert gas is passed through the sample and diluent (silica product and/or metal oxides) with gradually increasing temperature. Gases are evolved from the sample and are oxidized by oxygen supplied to the gas stream as it enters the second hot zone. The gases produced, carbon dioxide, sulfur dioxide, nitrogen dioxide, and water provide, after analysis, concentration versus time and/or temperature profiles for the pyrolysis gases produced from the substance being tested. Integrating the evolved gas profiles and relating them to the amount of carbon, hydrogen, sulfur, and nitrogen produced by pyrolysis with time data provides information similar to that of a thermal gravimetric analysis (TGA) experiment, in which samples are weighed as gases evolve. In addition, this provides information on the nature of the elemental composition of the volatile pyrolysis products.

A new multi-tube horizontal split combustion furnace made with two to six or more tubes has been designed and is incorporated into the system. A prototype version contains four combustion tubes and the temperature may be increased or ramped over a wide range of temperatures. However, 2° C. to 10° C., and preferably 3° C. per minute are the preferred rates of increase. The furnace, mass flow controllers for the inlet gases, pressure transducers and regulation system, stepper motor for cell movement, and a number of relays and the whole system may be controlled from one or more micro computers.

The furnace includes a second hot zone with oxidizing tubes, after each of the combustion tubes, containing tungsten trioxide, zirconium dioxide, a metal, or other metal oxide catalysts, heated to approximately 1050° C. The catalysts oxidize any gases that are not already in their highest oxidation state. Additionally, the second hot zone maximizes the sulfur dioxide concentration relative to sulfur trioxide. The second hot zone also assures a constant temperature for the emerging gas. The catalyst preferably does not interact, absorb or re-emit the evolved gases at different temperatures. The catalyst may absorb or emit the evolved gases at the same temperature.

Each combustion train in the new multi-tube furnace is fitted with an oxygen inlet between the two hot zones. That permits the system to be used in a pyrolysis mode, with an inert gas flowing through the system. The pyrolysis gases are all converted to oxides (carbon dioxide, nitrogen dioxide, sulfur dioxide, and water) in the second hot zone. Quantitative pyrolysis experiments, as well as oxidation experiments, can be conducted in any one or all of the combustion trains. The analyses can be completed by analyzing products of the organic compounds and other gases after they pass through the second hot zone using tungsten trioxide, zirconium dioxide, or other metal or metal oxide as an oxidation catalyst. The use of the second hot zone to oxidize the pyrolysis gases simplifies quantitative analysis of the gaseous pyrolysis mixture.

The split tube design allows removal and repacking of the sample tubes. The second hot zone tube is for catalytic conversion and catalyst tubes do not have to be repacked each time a new sample is analyzed.

The thermocouples that control the furnace are located in the combustion tubes and are embedded in the samples during the experiment. Employing a measuring thermocouple embedded in the samples ensures accurate sample temperature and controls furnace temperature. This thermocouple, used as the control thermocouple, provides a more even temperature ramp. The thermocouple can sense an exotherm and call for reduced heating sooner than a thermocouple mounted externally on the combustion tube.

The gases pass through a newly designed gas flow cell for analysis by a fourier transform infrared (FTIR) spectrometer. The gas cell is designed to take full advantage of the elliptical, almost cone-shaped, infrared light beam produced by FTIR spectrometers. The cell contains approximately one-third less gas volume than a conventional cell, and at the same time produces an infrared spectrum of the same intensity as a conventional infrared gas analysis cell of the same length and diameter.

Since the cell contains one-third less volume than a conventional gas cell, the clearing time is about one-third shorter. The cell tapers inward from the ends to the middle. This design shows some interesting flow patterns which might cause the clearing time of the cell to vary as a function of the angle of a directed flow inlet gas stream. At certain inlet angles the cell clearing time is significantly less relative to a non-directed inlet flow. These same inlet angle experiments were also carried out on a non-tapered gas cell that was identical to the above cell, except for the taper and cell volume. The cell clearing time was again found to be a function of the angle of the inlet gas stream. Thus, the directed flow modification is an important feature that also can be incorporated into conventional gas cells.

The properties of smaller volume and shorter clearing time due to the smaller volume and the directed flow make the tapered cell desirable for a wide variety of infrared gas cell applications.

The cell body can be fabricated from glass, steel, or a variety of polymeric materials in any length that will fit in a FTIR cell compartment. Any type of infrared window material (NaCl, $CaF_2$, KBr, $BaF_2$, CsI, CsBr, KRS-5, ZnSe, AgCl, Intran-2 or fused silica) may be attached through any conventional state-of-the-art techniques, such as a screw cap with seals threaded onto glass, metal, or plastics or to plastic threaded material snapped around the cell; metal or plastic rims (one behind a flange on the cell) screwed together with the window and seals between the rims.

The cell inlet and outlet can be fitted with simple tubulations at angles from 0° to 360° relative a long axis of the cell for flow through applications. Tubulation on an inside of a cell inlet can be directed at the best angle to give minimum clearing time. Septa for injection of gases directly into the cell, stopcock closures, or different fittings attach a variety of plastic or metal tubing to the cell.

The cell can be heated by a simple heat tape, by a controlled, enclosed heater mounted as an integral part of the cell, or by a number of other state-of-the-art heating methods.

The cell can be fabricated for use at medium or high pressures.

"Beam conforming cells" have been designed for older infrared instruments in which the beam emerged from the instrument in a rectangular shape. However, those differ significantly from the functional shape of the present cell.

A multi-cell holder has been designed to position one of four gas cells in the spectrometer beam for analysis normally every 15 seconds. A longer or shorter analysis timing sequence may be used. A stepper motor with a worm drive train moves the cell holder plate on command from a timer or a computer command. The movable cell holder may be adapted to any infrared instrument currently manufactured.

A mass flow controlled gas mixture is introduced to the combustion tubes. The pressure in the system is measured with a pressure transducer. A pressure regulation system on this instrument is used to keep the pressure in each gas cell constant.

The information obtained from the new instrumental system includes pyrolysis data on the amount of carbon, hydrogen, sulfur and nitrogen lost as the temperature of the sample is increased. That information is useful from the single or multi-tube furnace system. The evolved gas information is integrated to provide information similar to that obtained from thermal gravimetric analysis. In thermal gravimetric analysis (TGA) the sample is placed on a sensitive balance and is heated. The weight loss is measured as a function of temperature. In the present pyrolysis technique, the evolved gases are quantitatively measured and integrated over time to provide information on the amount of sample lost with time. The profiles resemble those produced in a TGA experiment, except that instead of mass the elemental composition of the carbon, hydrogen, nitrogen and sulfur lost by oxidation or pyrolysis is obtained.

A description of the present pyrolysis technique is a controlled-atmosphere programmed-temperature oxidation evolved gas analysis (CAPTO-EGA).

A preferred furnace has first and second hot zones. Multiple tubes extend between the first zone and the second zone. A catalyst is positioned in the tubes in the second zone. Sample-diluent mixtures are packed in parts of the tubes in the first zone. Gas flows into the inlets of the tubes in the first zone and flows through the samples, entraining pyrolysis gases from the samples. An oxygen source connected to the gas introduction means flows oxygen into the tubes for oxidizing the pyrolysis gases before and as the gases flow through the catalyst in the second hot zone. Outlets of the tubes are connected to gas analyzer cells for supplying oxidized pyrolysis gas to the cells, and exhaust lines connected to the cells for flowing gas out from the analysis cells.

A preferred gas supply is an oxygen source. A mass flow controller is connected to the oxygen source. A pressure transducer is connected between the mass flow controller and the tube for measuring pressure as the mass flow controller supplies oxygen to the inlet of a tube.

Plural mass flow controllers and plural transducers are each connected in parallel between an oxygen tank and distinct tubes.

Another embodiment has a source of inert gas and inert gas mass flow controllers connected to the inlets of the combustion tubes for supplying inert gas alone or in combination with oxygen to the combustion tubes.

Plural inert gas mass flow controllers are each connected in parallel between the source of inert gas and the inlets of the tubes.

Preferably the tubes are horizontal tubes, and the furnace is divided by a vertical wall into two heated zones.

In a preferred embodiment, an oxygen relay is connected to each mass flow controller and to an intermediate portion of a tube for supplying oxygen to an intermediate portion of the tube and to pyrolysis gases from the sample before the gases pass into the catalyst.

Preferably one relay is connected to each mass flow controller for receiving oxygen therefrom. A first oxygen supply line is connected between each relay and each pressure transducer connected to the inlet of each tube. A second supply line is connected between each relay and an intermediate portion of each tube for supplying oxygen to each tube between the sample and the catalyst.

Sample thermocouples extend through inlets of each tube into the sample packed in the tube for controlling furnace temperature in the first hot zone.

Catalyst thermocouples are inserted through outlets of the tubes into catalysts within the tubes for controlling temperature in the second hot zone of the furnace.

Plural cells are each connected to a tube extending from an outlet of the combustion tube.

In a preferred form of the invention, the gas analyzer cells are aligned parallel and are mounted on a slide. A motor moves the slide transversely. An infrared light beam source projects an infrared light beam through the cells. A detector aligned with the source on an opposite side of the slide receives light projected through the cells. The motor moves each cell into alignment and out of alignment with the infrared light beam in a predetermined sequential relationship.

Each cell has a tapered body which is relatively wide at the top, relatively narrow in the middle, and relatively wide at the bottom. A cell window forms the top of the cell, and a second cell window forms a bottom of the cell. A cell inlet is connected to a wall of the cell near the upper cell window, and a cell outlet is connected to a wall of the cell near the lower cell window. The inlet and outlet are directly across from one another or any angle to each other.

The tapered cell body is preferably a truncated, generally conical upper cell wall and a truncated, generally conical lower cell wall joined medially in a small waist portion.

The preferred gas inlet is a tube which extends through the upper cell wall at an angle of from about 0° to about 30° from the cell window. Preferably the inlet has an open end which points upwardly or toward the near end of the cell at about 0° to 60° to a vertical direction. An angle of up to about 90° is useful; about 0° to 30° is preferred.

The inlet tube is aligned with the cell wall between a tangential and a radial position for swirling and purging gas from within the cell.

Gas is flowed angularly into a top of a cell and downward through a converging upper portion of the cell, and subsequently downward through a diverging lower portion of the cell and out through the cell outlet at the bottom of the cell.

In a preferred embodiment, the combustion tubes have removable first combustion sections which separate from the second catalyst sections. The combustion sections may be withdrawn and repacked with sample material.

The preferred method of quantitatively analyzing multiple samples includes packing samples in first tube sections and packing a catalyst in second tube sections. The first and second tube sections are placed in horizontal communicating alignment in a furnace having a first hot zone which receives the first tube sections, and a second hot zone which receives the second tube sections. The first hot zone is heated with a gradually increasing temperature, and heating the second hot zone is held at a constant elevated temperature. Gas is introduced into an inlet of each tube. Preferably, in oxidative mode, the gas contains at least 50% oxygen. Heated resultant pyrolysis gases from the sample are entrained within the first tube section, while partially oxidizing the entrained gases. Oxygen may be supplied to the tubes between the sample and catalyst and mixing oxygen with the entrained pyrolysis gases, in pyrolysis mode the gases are heated and oxidized in the heated catalyst within the second tube sections, completing oxidation of the gases. Gases flow out of outlets of the second tube sections and into inlets in plural gas cells connected separately to the outlets of the second catalyst-holding tube sections. Gas flows through the gas cells and is released gas from the gas cells under pressure regulation. The cells are selectively moved into alignment with an infrared beam, and influence on the infrared beam by gas within the cells is sensed with an electronic detector. Other detectors may be used, for example a Raman spectrograph. Non dispersive infrared detectors, mass spectrometry or gas chromotography may be used in lieu of the gas cell analysis for the detection of products. Temperature within the first hot zone is raised at a slow rate of increase, and sequentially positioning the cells within the infrared light beam and detector during the increase in temperature in the first hot zone determines oxidized pyrolysis gases released from the samples and entrained and oxidized, and thereby determines content of the sample.

Preferably the increasing temperature in the first hot zone comprises increasing temperature at a rate of about 2° C. to 10° C. or about 3° C. per minute, while supplying an inert gas with the oxygen to an inlet of each first tube. The rate is chosen so that the products are released at different times and so that exothermic reactions are controlled or avoided. These and further and other objects and features of the invention are apparent in the disclosure, which includes the above and ongoing written specification, with the claims and the drawings.

DETAILED DESCRIPTION OF THE DRAWINGS

Figure 1:
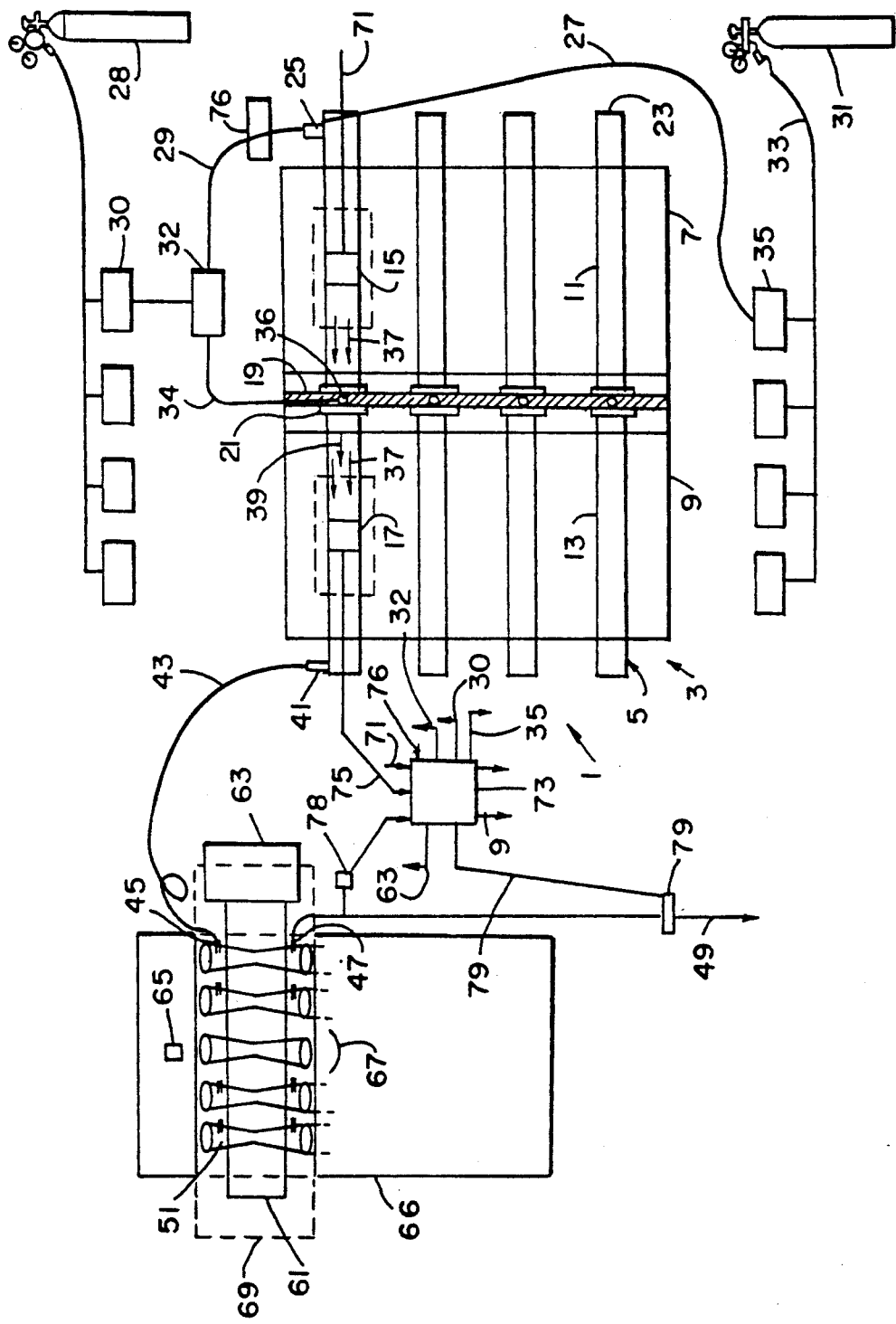
FIG. 1 is an overall system schematic drawing.

Referring to FIG. 1, a sample analysis system of the present invention is generally referred to by the numeral 1. The system has a furnace 3, which holds horizontal tubes 5, in this case four. The furnace is divided into two hot zones 7 and 9. Tubes 5 are divided into sections 11 and 13. First sections 11 hold a sample 15. Second sections 13 hold a catalyst 17. The hot zones are divided by an insulated wall 19, which includes plural tube connectors 21, as will later be described. Each tube section 11 has an inlet 23, on which is provided a gas supply connector 25. Gas is supplied through separate supply tubes 27 and/or oxygen is supplied through supply tubes 29 to separate inlets 23 of the tubes.

When an inert gas is used, an inert gas such as argon from a source 31 is supplied on line 33, which is connected to individual mass flow controllers 35, each of which is connected to a line 27, and each line 27 is connected to one inlet 23 of a sample tube 11. When oxygen is used to the exclusion of, or in addition to, the inert gas, oxygen is supplied from a source 28 through individual mass flow controllers 30 to the oxygen supply line 29 and the input connection 25 on the inlet 23 of each of the sample tubes.

All or part of the oxygen may be supplied through a relay 32 to a supply line 34, which is connected to an individual supply port 36 between the tubes. In a preferred embodiment, all oxygen is introduced either through the connections 25 or through the supply ports 36. Oxygen is intermingled with evolved and entrained gases 37, and the oxygen 39 fully oxidizes the entrained pyrolysis or partially oxidized gaseous products 37 in the catalyst 17 within each tube. The oxidized gases flow out through the outlet 41 of each tube 5, and through a conduit 43 to an inlet 45 of a gas cell. The gases then flow out through an outlet 47 to an exhaust 49.

Figure 2A:
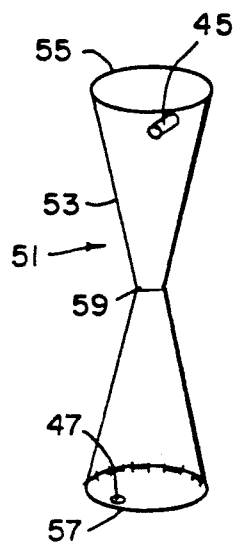
FIGS. 2A and 2B show a preferred gas cell.
Figure 2B:
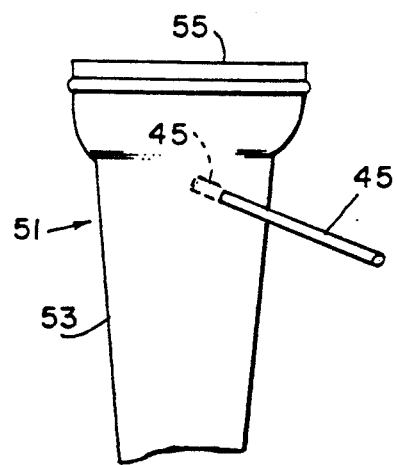

As shown in FIGS. 2A and 2B, each cell 51 has tapered upper and lower body portions 53, which taper uniformly inward from the cell windows 55 and 57 to a narrow central throat portion 59. The inlet 45 extends through the upper cell wall 53 at an angle of about 0° to 60° from a vertical axis of the cell and is aligned with the cell wall 53 between a tangential and radial position.

Because the cell is tapered, it reduces volume while still allowing maximum interaction of gas with the light beam within the cell.

As shown in FIG. 1, each cell 51 is mounted on a movable slide 61, which is driven by a motor 63 to position each cell sequentially and at timed intervals in alignment with an infrared light beam schematically indicated at 67. A spectrograph receiver schematically shown at 65 receives the light which interacts with the gas within the cell 51 and indicates the gas content and quantities of gas within the cell. The preferred form of a gas detector is a Fourier transform infrared detector (FTIR), of which the electronics and the interferometer are generally indicated in the box 66 attached to the light beam source 67 and the detector 65.

The entire slide 61 is enclosed in a heated compartment 69 to maintain the cells at constant temperature.

In a preferred embodiment of the invention, a thermocouple 71 is embedded centrally in the sample 15 to control heat in zone 7 through a processor 73. Heat in the first hot zone 7 is reduced, for example, when thermocouple 71 senses an exothermic reaction within the sample. The processor programs and controls heat in the first and second hot zones 7 and 9, and receives information from the thermocouple 75 which is mounted in each catalyst pack. The processor also controls the mass flow controllers 35 and 30 and relay 32, and receives inputs from pressure transducer 76, which is connected to the gas inlet 25. Processor 73 also receives information from pressure transducer 78 and controls pressure regulation valve 79. The processor also controls the timing and operation of motor 63, which moves the cells into and out of alignment with the FTIR detector.

Figure 3:
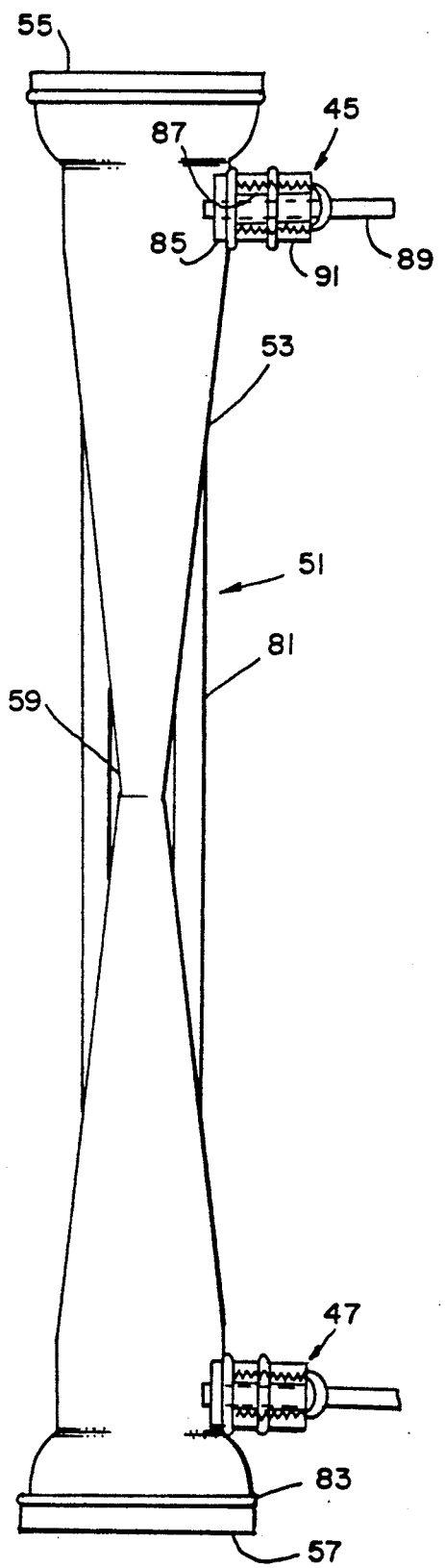
FIG. 3 shows further details of a preferred gas cell.
Figure 4:
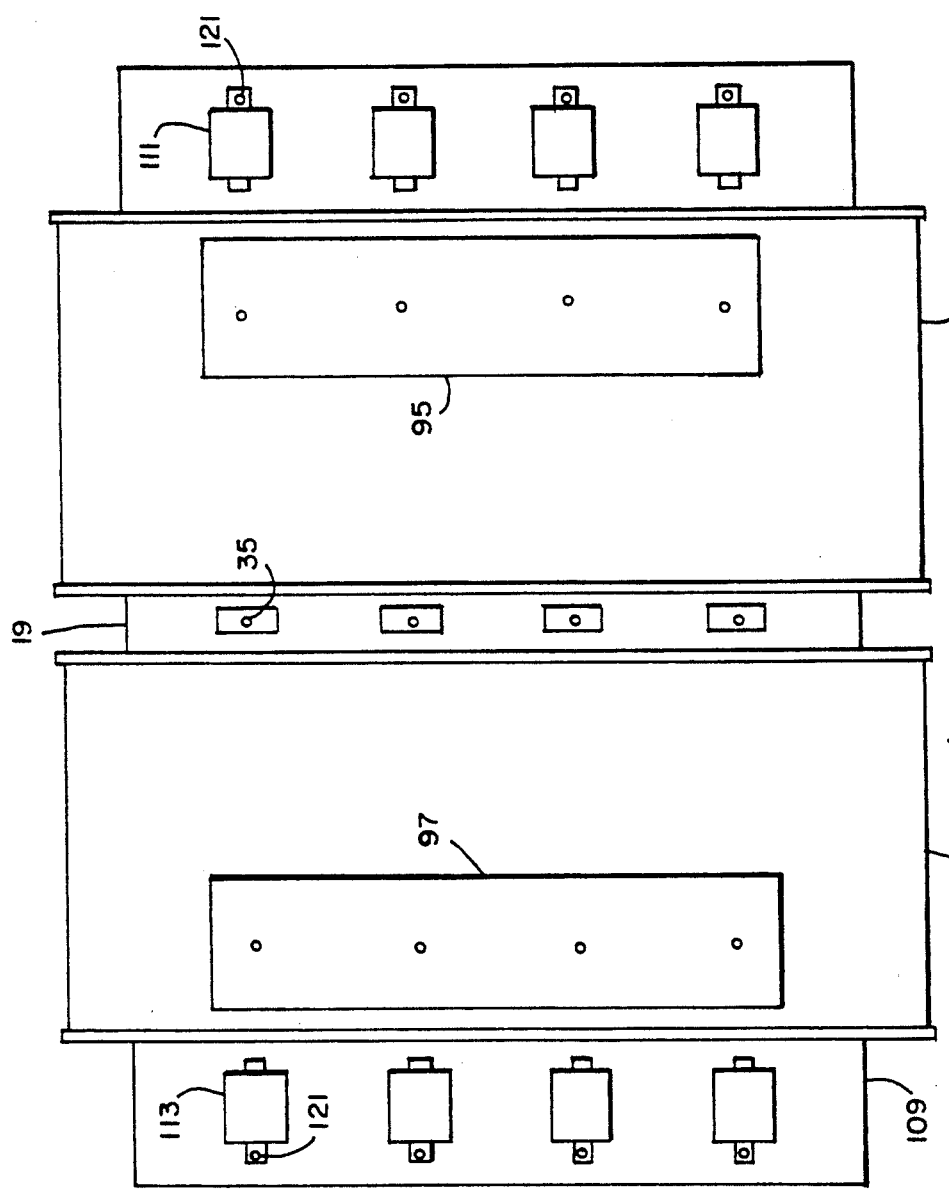
FIG. 4 is a top view of a preferred furnace.

As shown in FIG. 3, the narrow waist 59 of tube 51 is supported by glass rods 81, which are attached to the walls of the upper and lower sections 53.

The calcium fluoride windows 55 and 57 are bonded to the two bodies or are attached by brackets, which are not shown. O-rings 83 seal the cell ends in the enclosure.

Inlets and outlets may be formed as tubes extending from the cells. As shown, inlet 45 and outlet 47 are made of similar structures. A 5/16" or other hole is made in the end of each section 53. A base 85 is bonded in the opening, and a male connector 87 extends outward therefrom. A ¼" tube 89 is inserted through a ¼" O-ring, and a cap 91 is threaded onto the connector 87.

In a preferred form of the furnace 3, as shown in FIGS. 4-7, a base 93 forms a support for the furnace. The furnace is formed with separate sections 7 and 9, which are separately heated by heaters 95 and 97.

The furnace sections have identical construction. Each has a box 101 covered by a cover 103, which is held tight by clamps 105. Handles 107 are used to lift the cover around hinges 109. Lower heaters 99 are identical to the upper heaters. The sections 7 and 9 are separated by bracket 115, which supports a central tube connector 117 with an oxygen fitting 119. Tubes are removable from the furnace sections by opening the covers 103 and pulling the T-handles 121 and releasing the tubes, whereupon tube sections such as sample tube sections 11 may be removed and replaced.

Figure 6:
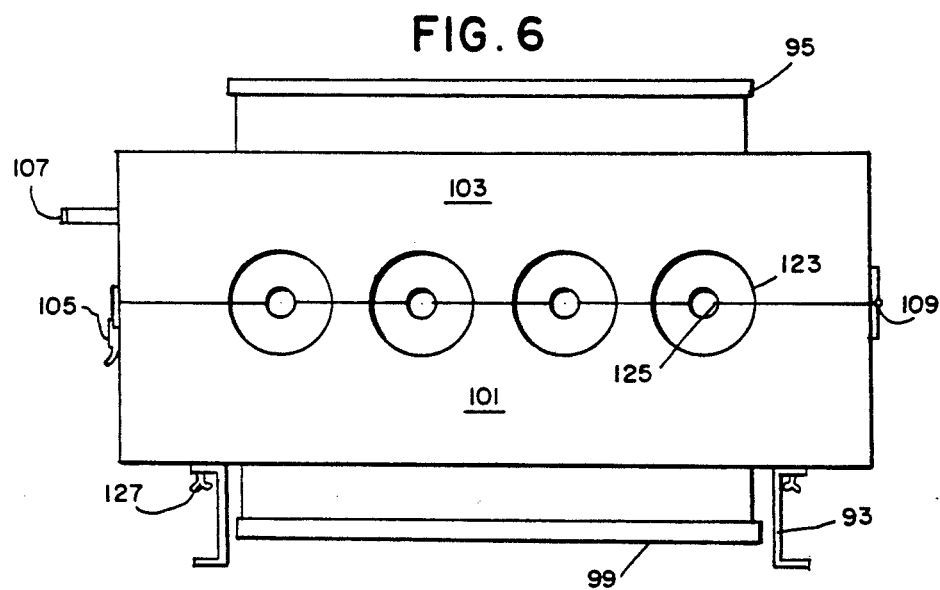
FIG. 6 is a side elevation of the furnace shown in FIGS. 4 and 5.
Figure 7:
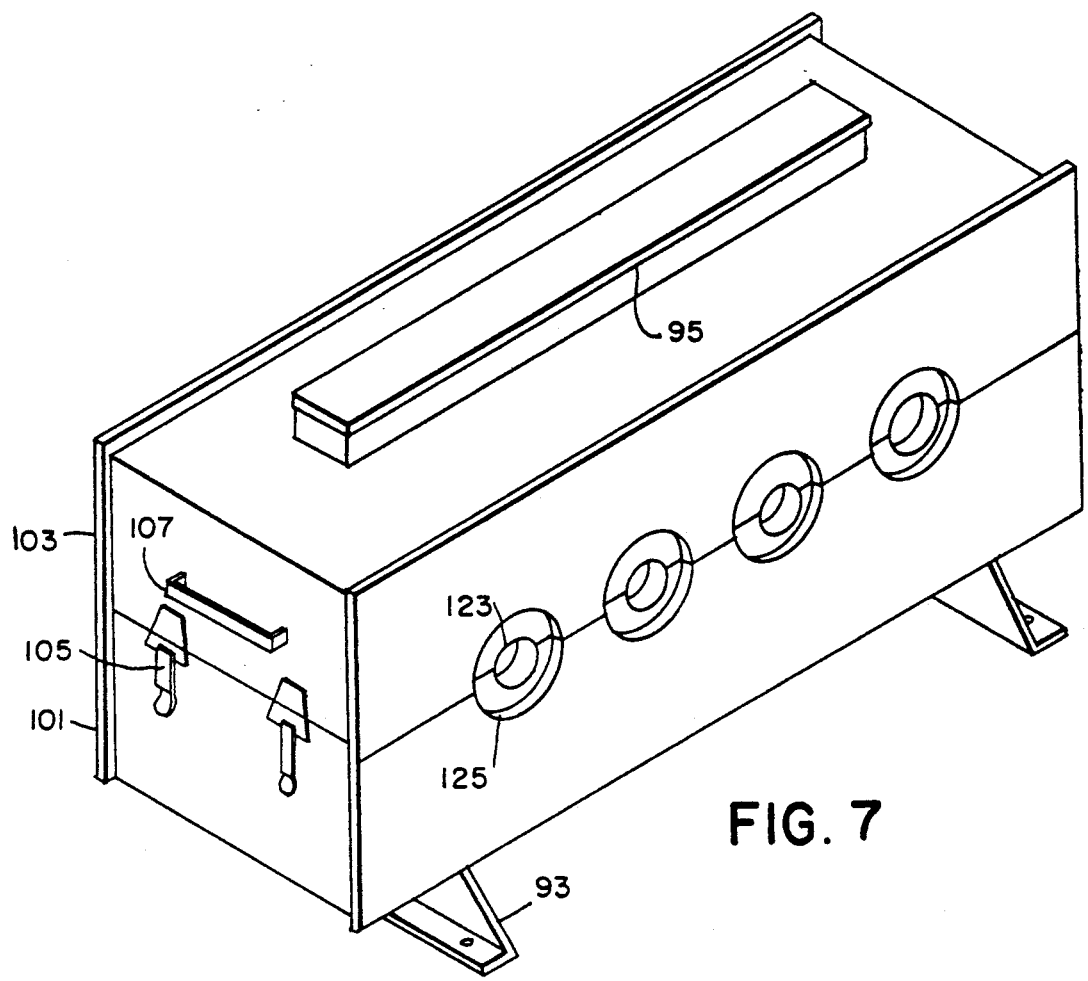
FIG. 7 is a perspective view of one furnace section.

FIG. 6 shows the side elevation of the furnace box 101 with openings 123 for receiving the tubes, and internal small openings 125 which extend through the central mounts 117. The bases 93 are shown as identical brackets connected to the lower furnace boxes by thumb screws 127.

Figure 5:
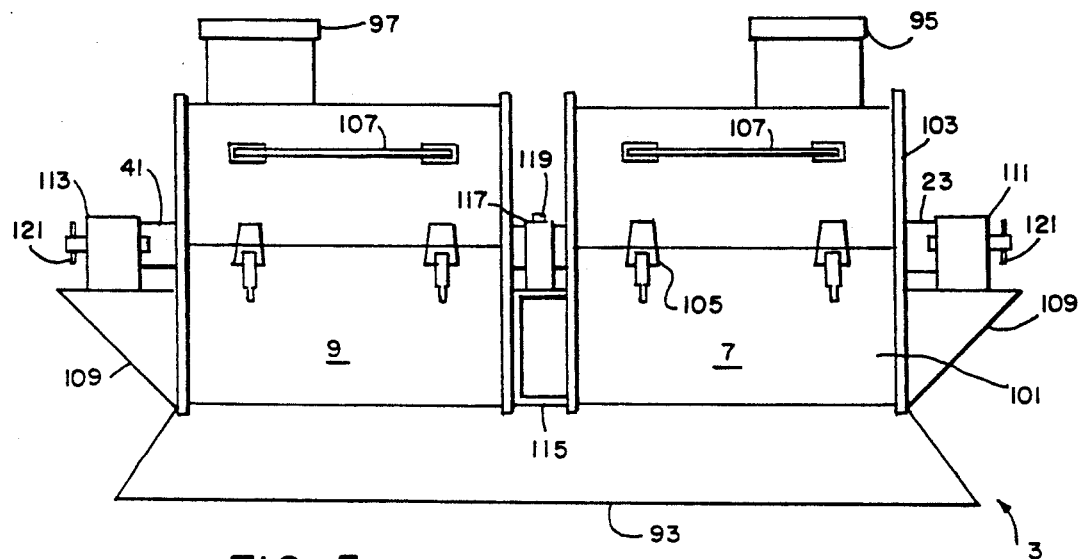
FIG. 5 is a front elevation of the furnace shown in FIG. 4.
Figure 8:
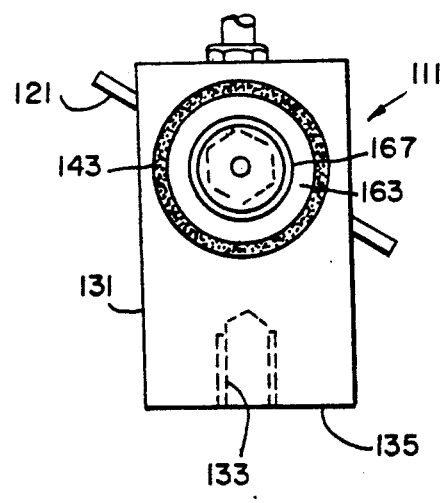
FIG. 8 is an end elevation of an end fitting used to hold tube sections in the furnace.
Figure 9:
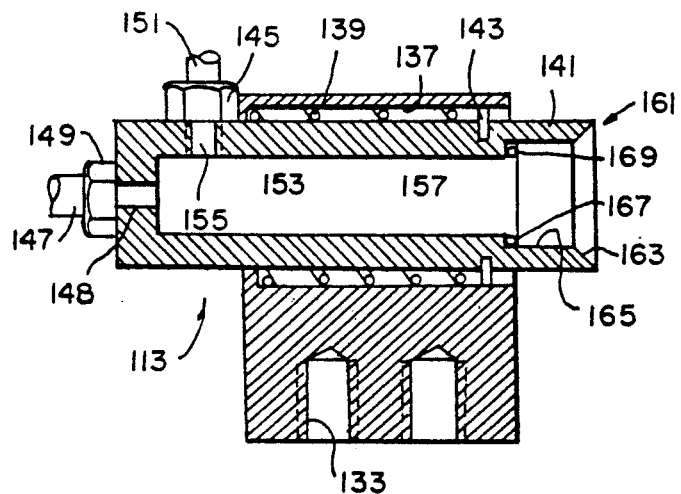
FIG. 9 is a cross-sectional elevation of the end fitting shown in FIG. 8.
Figure 10:
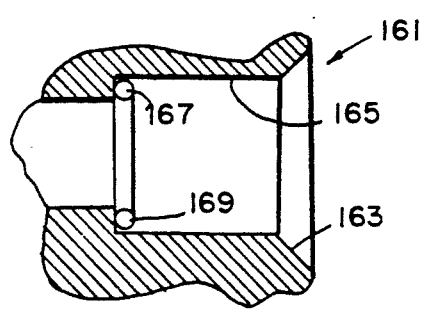
FIG. 10 is a detail of the end fitting shown in FIG. 8.

As shown in the details of FIGS. 8, 9 and 10, the identical end brackets 111 and 113 are formed with rectangular support bodies 131, having drilled and tapped openings 133 for mounting the bases 135 of the bodies 131 on the cantilevered supports 109 shown in FIG. 5.

The blocks have bores 137 which receive springs 139 and sliding barrels 141. A retainer 143 traps spring 139 in the bore 137. A fitting 145 prevents movement of the barrel 141 outward from the bore. The barrel is supplied with a T-handle 121, which is connected to shaft 147. Shaft 147 is connected by threads 148 to an end of the barrel 141. A lock nut 149 threaded on the shaft 147 secures the shaft-barrel connection. Gas tube 151 has a threaded connection 153 with the barrel. An opening 155 in tube 151 communicates with the lumen 157 of the sliding barrel 141.

As shown in FIG. 9 and the detail in FIG. 10, each sliding barrel 141 has a tube end receiver 161 with a chamfered opening 163 leading to a cylindrical wall 165 to receive a tube end in a slip-fit. A compressible neoprene 0-ring 167 rests against radial wall 169 to seal the end of an inserted tube against the wall. To remove or insert a tube, handle 121 is grasped and pulled, pulling shaft 147 and barrel 141 to the left, as shown in FIG. 9, whereupon the tube end 23 or 41 may be slid outward from the cylindrical wall 165.

Figure 11:
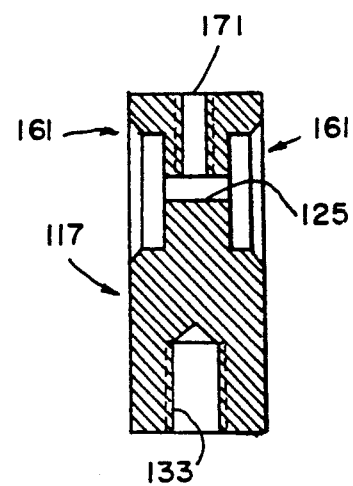
FIG. 11 is a detail of a tube interconnection fitting.
Figure 12:
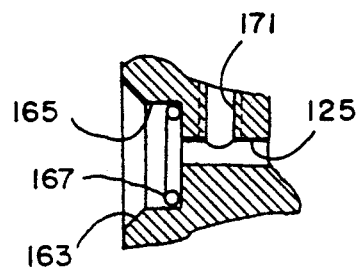
FIG. 12 is a detail of the fitting shown in FIG. 11.

As shown in FIG. 11, the central fitting 117 has opposite tube end receivers 161, which is shown in FIG. 12 to be similar to the receiver 161 shown in FIG. 10. The fitting 117 has two drilled and tapped bolt-receiving openings 133 for attaching the fitting. Oxygen-admitting channel 171 connects with opening 125, which passes between receivers 161 to admit oxygen to the gas flowing through opening 125.

In a preferred embodiment of the invention, the furnace is made of stainless steel sheet material lined with high temperature insulation. The tubes are stainless steel tubes, or more desirably, heat resistant glass, ceramic, or quartz tubes.

The preferred gas cell is made of stainless steel or, more desirably, heat-resistant glass, polymeric materials, quartz or ceramic. A preferred cell is about 18 or 20 cm long and has internal diameters of about 25 mm at the ends and 8 mm at the center.

A metal deposited upon the internal walls of the tapered gas cell body makes these surfaces highly reflective and increases the signal sent to the FTIR detector through an empty gas cell compared to the signal obtained through a gas cell without metal disposition on the internal cell walls.

The effect may be maximized (maximum reflective interaction of the infrared light beam through the gases being analyzed) by positioning a tapered gas cell, which is already aligned in the infrared beam, at a certain point between the entrance and exit windows of the infrared instrument cell compartment, or by slightly misaligning the cell and beam to promote reflection. The effect provides an increase in the interaction of the infrared light beam with a given concentration of gas, and should be of general utility as a gas cell for detecting somewhat lower concentrations of gases compared to a tapered gas cell without metal deposition on the internal cell walls.

Figure 13:
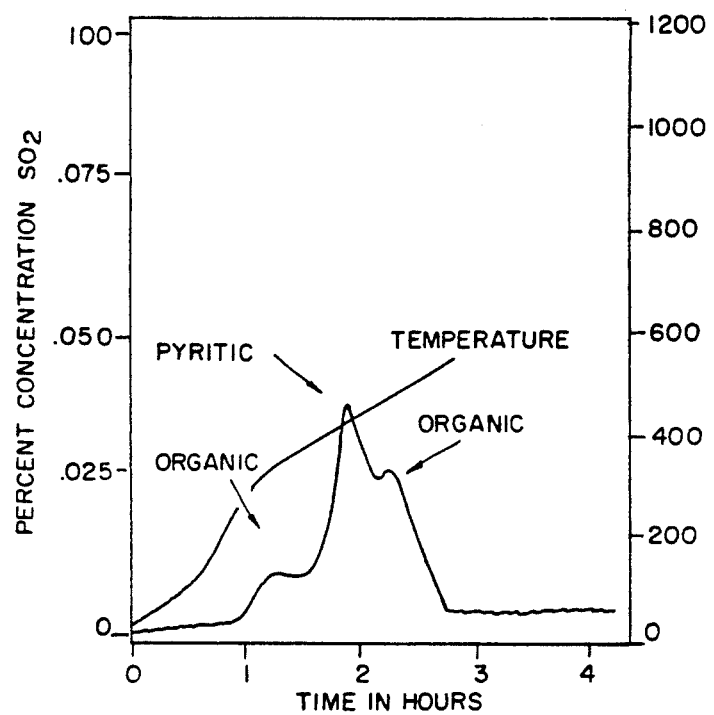
FIG. 13 is a graph of $SO_2$ peaks produced from 10% $O_2$ experiments.

FIG. 13 shows the sulfur dioxide evolution profile resulting from a coal sample thoroughly mixed with tungsten trioxide as diluent and oxidized under the previous TODS conditions of about 100 ml/min. of 10% oxygen in Argon and a linear increase in temperature of 3° C./min. Note that the peak produced from pyrite in the coal appears between the two major peaks produced from the organic sulfur in the coal and is not well resolved from either peak.

Figure 14:
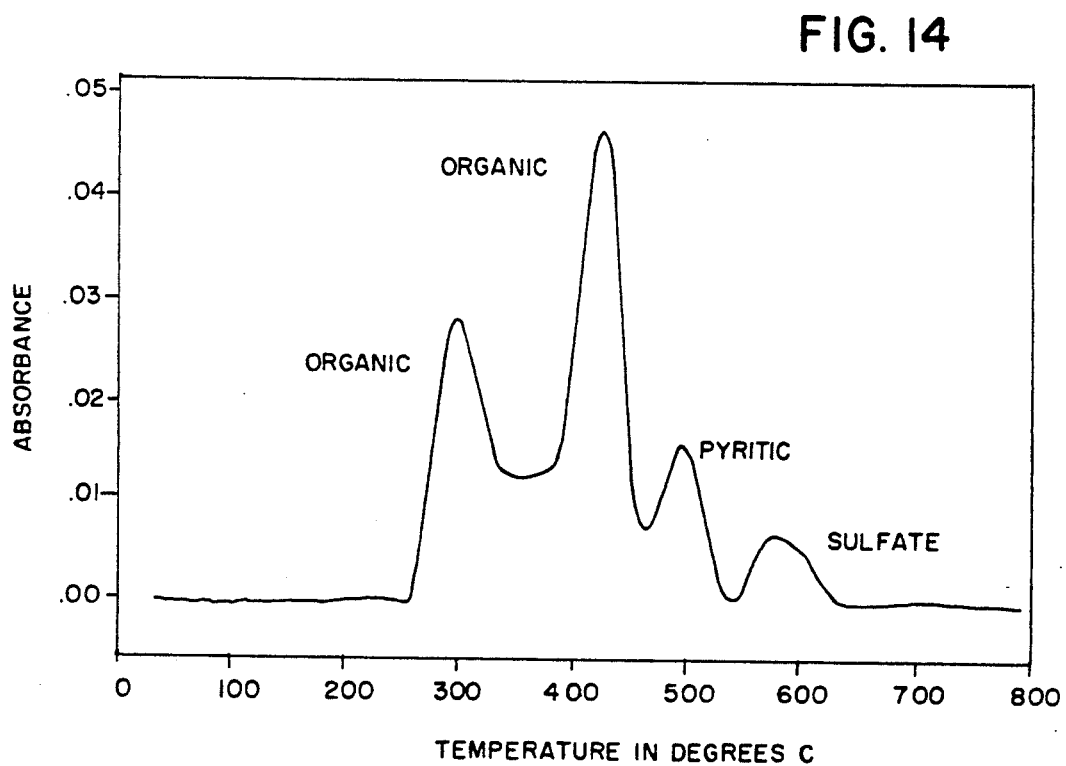
FIG. 14 is a graph of $SO_2$ peaks from 100% $O_2$.

FIG. 14 shows the sulfur dioxide evolution profile resulting from a coal sample thoroughly mixed with celite and oxidized with about 100 ml/min. of 100% oxygen and a linear increase in temperature of 3° C./min. Note that the peak produced from pyrite in the coal appears after the second major peak produced from organic sulfur in coal. Also note that the separation between the pyritic peak and the peak resulting from the second major occurrence of organic sulfur in coal are significantly improved, permitting quantitative estimation of the various types of sulfur in coal.

Table 1 shows sulfur dioxide evolution peaks observed from coal and other substances to a specific structural feature.

EXAMPLE 1

A finely divided, dry, representative sample (50-200 mg with a particle size of −60 Mesh or smaller) is weighed and thoroughly dispersed in approximately 0.6 g of celite and redried for one hour in vacuum at 105° C. The samples are positioned in the combustion tubes between small wads of quartz wool that has been heat treated at 1100° C. for one hour. Any voids in the combustion or catalyst tubes are reduced by positioning quartz rods in the tubes. These rods are also held in place using heat treated quartz wool. The tubes are positioned horizontally in the furnace and control thermocouples are embedded into the sample and catalyst pack. A flow of approximately 100 ml/min. of 100% oxygen is directed through each tube in the first hot zone of the furnace and the FTIR, cell positioner, and data system are set up for data collection. The temperature of the second tube containing the catalyst is quickly raised to at least 1050° C. A hot zone and data collection is initiated. The run is allowed to continue for approximately 5.5 hours until a temperature of at least 1050° C. is obtained. All calculations and graphic hardcopy are completed using the FTIR data system and printer/plotter. Each of the sample tubes in the first hot zone can be used as described above, or any one or more can be used simultaneously to analyze in the pyrolysis mode described below. Any tube in the first and second furnace hot zones can be ramped with a similar or different temperature program. Additionally, the gas flow and pressure control for any of the four sample trains can be the same or dissimilar. The complete operation of the system, including temperature control and monitoring, gas flow, pressure control and monitoring, gas cell positioning unit, and data acquisition, may be under the control of one or more microcomputers.

EXAMPLE 2

Sample preparation, dilution with celite, and insertion into the combustion tube is completed as described above. Alternatively, for pyrolysis studies the undiluted sample can be placed in a small ceramic, quartz, or metal boat and inserted into the combustion tube. The thermocouple is positioned close to the sample as the combustion tube is inserted into the furnace. The second tube containing the catalyst is positioned in the second hot zone and the temperature raised quickly to at least 1050° C. An inert gas flow, normally 50 ml/min. of Argon or helium, is established in the tubes in the first furnace hot zone and normally, a flow of 50 ml/min. of oxygen is established at the inlet of the second tube to continuously oxidize material lost from the sample as the first tube is exposed to a linear temperature increase, normally of 2°-10° C./min. The data system and gas cell positioner are powered up and the temperature ramp and data collection are initiated. A run is allowed to continue for approximately 5.5 hours until a temperature of 1050° C. is attained (temperature ramp and final temperature required varies with the sample and may be shorter or longer).

A nonvolatile residue may remain in the first hot zone after the highest pyrolysis temperature desired has been attained. The system may be used in the oxidative mode described above to obtain further characterization of any residue. The furnace may be cooled to room temperature and the same sample tube exposed to an oxygen flow (100 ml/min.) directed into the first furnace hot zone as the temperature is increased in a linear ramp of 2°-10° C./min. or more, depending on the amount and type of residue remaining. The gas cells, cell positioner, and data system are all used as described above to complete the characterization of the residue.

While the invention has been described with reference to specific embodiments, modifications and variations of the invention may be constructed without departing from the scope of the invention, which is defined in the following claims.

I claim:

1. A furnace comprising first and second hot zones, a plurality of tubes each having separable sample-receiving and catalyst-holding sections in the first zone and the second zone respectively, a catalyst positioned in sections of the tubes in the second zone, and sample-receiving sections in tubes in the first zone, a gas supply for flowing gas into inlets of the sample-receiving sections of the tubes in the first zone, for flowing gases through the samples and entraining gases from the samples, the gas supply including an oxygen source selectively connected to the tubes between the first and second zones for selectively flowing oxygen into the tubes between the sections for oxidizing pyrolysis gases before and as the gases flow through the catalyst in the tubes in the second hot zone, gas conduits connected to outlets of the catalyst-holding sections of the tubes and connected severally to inlets of a like plurality of analysis cells for supplying oxidized gas to the gas analysis cells, and exhaust lines connected to the gas analysis cells for flowing gas out from the analysis cells, wherein the plural cells are aligned parallel to each other and are mounted on a slide, further comprising a motor for moving the slide transversely, and further comprising an infrared light beam source for projecting an energy beam through the plural cells, and a detector aligned with the source on an opposite side of the slide for receiving light projected through the plural cells, the motor and slide cooperating for moving each cell into alignment and out of alignment with the infrared light beam source.

2. The apparatus of claim 1, wherein the gas supply comprises a mass flow controller connected to the oxygen source and to the inlets of the tubes, a pressure transducer connected to the mass flow controller for receiving oxygen from the mass flow controller, measuring pressure and conveying oxygen to the inlet of each tube.

3. The apparatus of claim 2, further comprising plural mass flow controllers and plural pressure transducers, each connected in series from the oxygen source to one end of a sample-receiving section of one distinct tube.

4. The apparatus of claim 3, further comprising a relay connected to each mass flow controller for receiving oxygen therefrom, and first oxygen supply lines connected between each relay and each pressure transducer connected to the inlet of each tube for supplying oxygen to the inlet of each tube, and second supply lines connected between each relay and an intermediate portion of each tube for supplying oxygen to each tube between the sample and the catalyst.

5. The apparatus of claim 4, further comprising first thermocouples extending through inlets of each tube and into a sample packed in each tube for controlling furnace temperature increases in the first hot zone, and a monitoring thermocouple located outside of each tube.

6. The apparatus of claim 1, further comprising a source of inert gas, an inert gas mass flow controller connected to the source of inert gas and to an inlet of each sample-receiving section for supplying inert gas in combination with oxygen to the inlet of each sample-receiving section.

7. The apparatus of claim 6, further comprising plural inert gas mass flow controllers, each connected in series between the source of inert gas and an inlet of each tube.

8. The apparatus of claim 1, wherein the tubes are horizontal tubes, and wherein the furnace is divided by a vertical wall into a first hot zone and a second hot zone.

9. The apparatus of claim 6, further comprising an oxygen relay connected to a mass flow controller and connected to the tube between the sample-receiving and catalyst-holding sections for supplying oxygen between the sample-receiving and catalyst-holding sections and for mixing oxygen with pyrolysis gases from the sample before the gases pass into the catalyst.

10. The apparatus of claim 1, further comprising catalyst thermocouples inserted through outlets of the tubes into catalysts within the tubes for controlling temperature in the second hot zone of the furnace.

11. The apparatus of claim 1, wherein each cell has an elongated tapered body which is relatively wide at the top, relatively narrow in the middle compared to the top and bottom, and relatively wide at the bottom, a first cell window in the top of the cell and a second cell window in a bottom of the cell, a cell inlet connected to a wall of the cell near the first cell window, and a cell outlet connected to a wall of the cell near the second cell window.

12. The apparatus of claim 11, wherein each tapered body has a long truncated, generally conical upper cell wall and a long truncated, generally conical lower cell wall joined medially in a small waist portion.

13. The apparatus of claim 12, wherein the cell inlet is a tube which extends through the upper cell wall at an angle of from about 0° to about 60° from a vertical axis of the cell.

14. The apparatus of claim 12, wherein the cell inlet is aligned with the cell wall between a tangential and a radial position for swirling and purging gas from within the cell.

15. A method of quantitatively analyzing multiple samples, comprising providing plural sample tubes, packing samples in plural first sample tube sections, packing catalyst in plural second catalyst tube sections, connecting each of the sample tube sections with a catalyst tube section, placing the connected sample and catalyst tube sections in horizontal communicating alignment in a furnace having a first hot zone which receives the first tube sections, and a second hot zone which receives the second tube sections, heating the first hot zone to uniformly increasing temperatures, and heating the second hot zone to a constant elevated temperature, introducing gas into an inlet of each sample tube, the gas containing at least 50% oxygen, entraining heated resultant gases from the samples within the sample tube sections and partially oxidizing with the introduced gas, and mixing the introduced gas and the entrained resultant gases, oxidizing the entrained resultant gases in the heated catalyst within the catalyst tube sections, and completing oxidization of the entrained resultant gases and forming oxidation gases, flowing all of the gases out of outlets of the catalyst tube sections and into inlets in plural gas cells connected separately to the outlets of the second catalyst-holding tube sections, flowing all of the gases through the gas cells and releasing the gases from the gas cells under pressure regulation, selectively moving the gas cells into alignment with an infrared beam and detecting influence on the infrared beam by gas within the cells with an electronic detector, increasing temperature within the first hot zone at a slow rate of increase, and sequentially positioning the cells within the infrared light beam and detector during the increase in temperature in the first hot zone for determining gases released from the samples and entrained and oxidized, and thereby determining content of the sample.

16. The method of claim 15, wherein the increasing temperature of the first hot zone comprises increasing temperature at a rate of about 2° C. to 10° C.

17. The method of claim 15, further comprising supplying an inert gas with the oxygen to an inlet of each sample tube.

18. The method of claim 15, further comprising flowing gas angularly into a top of a cell and flowing gas downward through a converging upper portion of the cell and subsequently downward through a diverging lower portion of the cell and out through the cell outlet at the bottom of the cell.

19. A gas analyzing apparatus comprising plural gas cells aligned parallel and mounted on a slide, a motor for moving the slide transversely, an infrared light beam source for projecting an infrared light beam through the cells, and a detector aligned with the source on an opposite side of the slide for receiving light projected through the cells, the motor and slide cooperating for moving each cell into alignment and out of alignment with the infrared light beam source.

20. The apparatus of claim 19, wherein each cell further comprises a tapered body which is relatively wide at the top, relatively narrow in the middle compared to the top and bottom, and again relatively wide at the bottom, a first cell window forming the top of the cell and a second cell window forming a bottom of the cell, a cell inlet connected to a wall of the cell near the upper cell window, and a cell outlet connected to a wall of the cell near the lower cell window.

21. The apparatus of claim 20, wherein the tapered body has a truncated, generally conical upper cell wall and a truncated, generally conical lower cell wall joined medially in a small waist portion.

22. The apparatus of claim 21, wherein the cell inlet is a tube which extends through the cell wall at an angle of from about 0° to about 30° from the first cell window.

23. A combustion tube sample analyzing apparatus comprising a tube, a furnace for heating a sample-holding portion of the tube, and a thermocouple embedded in the sample within the tube and programmed control means responsive to the thermocouple in the sample for stopping furnace heating immediately upon internally sensing exothermic reaction in the sample.

* * * * *